US006974875B2

(12) United States Patent
Koch et al.

(10) Patent No.: US 6,974,875 B2
(45) Date of Patent: Dec. 13, 2005

(54) PROCESS FOR PREPARING INTERMEDIATES FOR THE MANUFACTURE OF DISCODERMOLIDE AND DISCODERMOLIDE ANALOGUES

(75) Inventors: Guido Koch, Riehen (CH); Olivier Loiseleur, Saint-Louis (FR); Gottfried Sedelmeier, Schallstadt (DE)

(73) Assignee: Novartis AG, Basel (CH)

( * ) Notice: Subject to any disclaimer, the term of this patent is extended or adjusted under 35 U.S.C. 154(b) by 199 days.

(21) Appl. No.: 10/466,728

(22) PCT Filed: Jan. 21, 2002

(86) PCT No.: PCT/EP02/00570

§ 371 (c)(1),
(2), (4) Date: Aug. 22, 2003

(87) PCT Pub. No.: WO02/057251

PCT Pub. Date: Jul. 25, 2002

(65) Prior Publication Data

US 2004/0073049 A1 Apr. 15, 2004

(30) Foreign Application Priority Data

Jan. 22, 2001 (GB) .............................................. 0101599

(51) Int. Cl.$^7$ ............................................ C07D 319/06
(52) U.S. Cl. ....................................................... 549/374
(58) Field of Search ......................................... 549/374

(56) References Cited

U.S. PATENT DOCUMENTS

| 5,789,605 A | 8/1998 | Kobayashi et al. |
| 6,096,904 A | 8/2000 | Smith, III et al. |

FOREIGN PATENT DOCUMENTS

| GB | 2 280 677 A | 2/1995 |
| WO | WO 98 48791 | 11/1998 |
| WO | WO 00 04865 | 2/2000 |

OTHER PUBLICATIONS

Arefolov, Alexander et al., "Studies toward the synthesis of (+)-discodermolide," Book of Abstracts, 216th ACS National Meeting, Boston, Aug. 23–27, 1998, ORGN–661 (1998).
Balachandran, Raghavan et al., "Increased sensitivity of the antiestrogen–resistant MCF–7/LY2 human breast carcinoma cell line to apoptosis induced by the novel microtubule stabilizing agent (+)-discodermolide," Breast J., vol. 4(6), pp. 409–419 (1998).
Burke et al., "An alternative route to the C(7)–C(13) subunit of erythronolide B via a hydropyran template," Tetrahedron Lett., vol. 28, No. 36, pp. 4147–4148 (1987).
Clark, David et al., "Studies on the alkylatin of chiral enolates: application toward the total synthesis of discodermolide," J. Org. Chem., vol. 58, pp. 5878–5879 (1993).

Donaldson, William et al., "Reactivity of (Pentadienyl)iron(1+) cations: effect of peripheral ligands on the regioselectivity of nucleophilic addition," Tetrahedron Letter, vol. 36(10), pp. 1575–1576 (1995).
Evans, David et al., "Chelation–controlled stannylacetylene additions to (–alkoxy aldehydes promoted by alkylaluminum halide lewis acids," Tetrahedron Letters vol. 40, pp. 4461–4462 (1999).
Evans, Philip et al., "The synthesis of a C9–C17 fragment of discodermolide," Tetrahedron Letters, vol. 34(50), pp. 8163–8166 (1993).
Filla, Sandra et al., "Synthesis of C1–C–8 and C–9–C24 fragments of (–)–discodermolide: use of asymmetric alkylation and stereoselective aldol reactions," Tetrahedron Letters, vol. 40, pp. 5449–5453 (1999).
Golec, Julian et al., "An approach to the synthesis of a C9—C15 Fragment of Discodermolide," Tetrahedron Letters, vol. 34(50), pp. 8167–8168 (1993).
Golec, Julian et al., "The synthesis of a C1–C8 lactone fragment of discodermolide," Tetrahedron Letters, vol. 34(50), pp. 8159–8162 (1993).
Hutchins R. O. et al., "Sodium borohydride in dimethyl sulfoxide of sulfolane. Convenient systems for selective reductions of primary, secondary and certain tertiary halides and tosylates," Tetrahedron Letters, No. 40, pp. 3495–3498 (1969).
Krishnamurthy, S. et al., "Synthetic applications of phenylselenenyl chloride additions. A simple 1,3–Enone transposition sequence," J. Org. Chem., vol. 45, pp. 2551–2553 (1980).
Marshall, James et al., "Synthesis of discodermolide subunits by SE2' Addition of nonracemic allenylstannanes to aldehydes," J. Org. Chem., vol. 63, pp. 817–823 (1998).
Misske, Andrea et al., "Asymmetric synthesis of seven–carbon segments of the phorboxazoles and (–)–discodermolide: complementary route from racemic trans–2, 4–dimethyl–8–oxabicyclo[3.2.1]oct–6–en–3–one," Tetrahedron, vol. 55, pp. 4315–4324 (1999).
Miyazawa, Masahiro et al., "Stereoselective synthesis of the C1–C7 segment of (+)-discodermolide," Chemistry Letters 1997, p. 1191–1192 (1997).
Miyazawa, Masahiro et al., Synthesis of the C8–C15 Segment of (+)-discodermolide, Chemistry Letters 1997, pp. 1193–1194.

(Continued)

*Primary Examiner*—Taofiq Solola
(74) *Attorney, Agent, or Firm*—Lydia T. McNally

(57) ABSTRACT

The invention relates to a process for the preparation of a substituted alkene of formula (I) wherein $R_1$, $R_2$ and $R_3$ are independently of each other a protecting group for a hydroxy group or hydrogen and $R_4$ is phenyl which is unsubstituted or mono- or disubstituted by alkoxy, which alkene constitutes an intermediate for the preparation of discodermolide and discodermolide analogues.

9 Claims, No Drawings

OTHER PUBLICATIONS

Myles, David et al., "The synthesis of discodermolide: C1 to C–21 connectivity and stereochemistry," Book of Abstracts, 211th ACS National Meeting, New Orlans, LA, Mar. 24–28, ORGN–112 (1996).

Nagasawa K., et al., "Total synthesis of preswinholide A. 2. Completion of the synthesis," Tetrahedron Letters, vol. 37(38), pp. 6885–6888 (1996).

Nerenberg, Jennie et al., "Total synthesis of the immunosuppressive agent (–)–discodermolide," J. Am. Chem. Soc., vol. 115, pp. 12621–12622 (1993).

Paterson I. et al. "Studies towards the total synthesis of the marine–derived immunosuppressant discodermolide: stereoselective synthesis of a C9–C24 Subunit," Synlett Letters, Spec. Issue, pp. 498–500 (1995).

Paterson, Ian et al., "Studies towards the total synthesis of the marine–derived immunosuppressant discodermolide; asymmetric synthesis of a C1–C8 (–lactone subunit," Chem. Soc. Chem. Commun., vol. 24, pp. 1790–1792 (1993).

Paterson, Ian et al., "Synthesis of (+)discodermolide and analogues by control of asymmetric induction in aldol reactions of ( –chiral (Z)–enals," Tetrahedron Letters, vol. 41, pp. 6935–6939, (2000).

Paterson, Ian et al., "Total synthesis of the antimicrotubule agent (+)–discodermolide using boron–mediated aldol reactions of chiral ketones," Angew. Chem. Int. Ed., vol. 39(2), pp. 377–380 (2000).

Rapoport, Henry et al., "(7–and (8–Desoxycodeine," J. Am. Chem. Soc., vol. 73, p. 2872–2876 (1951).

Smith A. B., et al., "Total synthesis of (–)–discodermolide," Journal of the American Chemical Society, vol. 117, pp. 12011–12012 (1995).

Smith, Amos B., "Gram–scale synthesis of (+)–discodermolide," Book of Abstracts. 219th ACS National Meeting, San Francisco, CA, Mar. 26–30, 2000, ORGN–290 (2000).

Smith, Amos et al., "Evolution of a gram–scale synthesis of (+)–discodermolide," J. Am. Chem. Soc. vol. 122, pp. 8654–8664 (2000).

Smith, Amos et al., "Total synthesis of immunosuppresants: unified straqtegies exploiting dithiane couplings and σ–bond olefin constructions," Acc. Chem. Res., vol. 31(1), pp. 35–36 (1998).

Ueno, Yoshio et al., "A radical deoxygenation of primary alcohols by use of tri–n–butyltin hydride–sodium iodide, and its application to a radical cyclization," Chemistry Letters, pp. 795–796 (1983).

Yang, Ge et al., "An alkylative strategy to the C–13 to C–21 sector of discodermolide," Tetrahedron Letters, vol. 35(9), pp. 1313–1316 (1994).

Yang, Ge et al., "The synthesis of the C–9 to C–21 sector of discodermolide: an efficient route to the C13–14 Z–trisubstituted alkene," Tetrahedron Letters, vol. 35(16), pp. 2503–2504 (1994).

PROCESS FOR PREPARING INTERMEDIATES FOR THE MANUFACTURE OF DISCODERMOLIDE AND DISCODERMOLIDE ANALOGUES

The invention relates to a process for preparing intermediates for the manufacture of discodermolide and discodermolide analogues and to the intermediates obtained during the process.

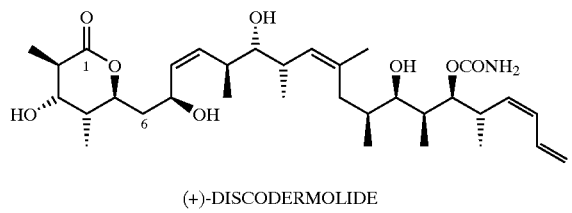

(+)-DISCODERMOLIDE (+)-Discodermolide is a polyketide natural product that was isolated from extracts of the marine sponge *Discodermolide dissoluta* by researchers at the Harbor Branch Oceano-graphic Institution [S. P Gunasekera et al., J. Org. Chem. 1990;55:4912–15 (published erratum appears in J. Org. Chem. 1991;56:1346)]. Discodermolide lacks obvious structural resemblance to paclitaxel, yet it shares with paclitaxel (the active substance in the drug Taxol®) the ability to stabilize microtubules. Paclitaxel has proven to be useful in treating some types of cancer in clinical practice. Discodermolide binds to tubulin competitively with paclitaxel and was shown to have utility against hyperproliferative disorders (see, e.g., WO 97/20835). Future development of discodermolide or structurally related analogues is hindered by the lack of a natural source that could provide greater amounts of the compound, since naturally occurring discodermolide is scarce and harvesting the producing organism presents logistical problems. Also lacking is a feasible synthetic route. Accordingly, there is a need for improved processes of manufacture of discodermolide and analogues thereof and for novel intermediates for such processes of manufacture which processes and intermediates enable the manufacture of commercially acceptable quantities of discodermolide and structurally related analogues.

The present invention relates to a process for preparing a substituted alkene of formula I

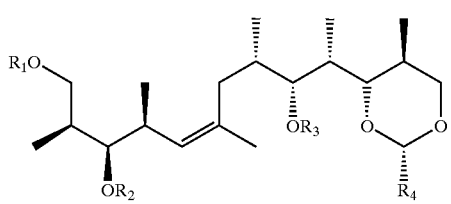

(I)

wherein $R_1$, $R_2$ and $R_3$ are independently of each other a protecting group for a hydroxy group or hydrogen and $R_4$ is phenyl which is unsubstituted or mono- or disubstituted by alkoxy, in which process a sulfonate of formula (II)

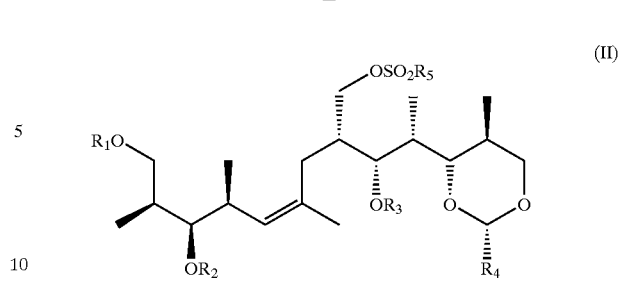

(II)

wherein $R_1$, $R_2$ and $R_3$ are all protecting groups for a hydroxy group which protecting groups can be identical or different, $R_4$ has the meaning as defined for the compound of formula I and $R_5$ is alkyl or aryl which is unsubstituted or substituted by alkyl, is reduced, e.g., by treatment with $NaBH_4$, $LIBH_4$, diisobutyl aluminium hydride, $LiB(ethyl)_3H$, Zn, tributyl tin hydride or, preferably, $LiAlH_4$, and afterwards, if desired, one, two or all protecting groups $R_1$, $R_2$ and $R_3$, in particular the protecting group $R_1$, are detached. Suitable reaction conditions for a reduction utilising $LiAlH_4$ are, for example, described in J. Org. Chem. 1980, 45, 2550 to 2551 or also J. Am. Chem. Soc. 1951, 73, on page 2874 (second Example described there). $NaBH_4$ can, for example, generally be employed in dimethyl sulfoxide or sulfolane at a temperature between 15° C. and 100° C., e.g. 25° C. or 85° C., and tributyl tin hydride generally in refluxing 1,2-dimethoxyethane (DME) in the presence of sodium iodid.

Furthermore, the present invention relates to a process for preparing a substituted alkene of formula I wherein $R_1$, $R_2$ and $R_3$ are independently of each other a protecting group for a hydroxy group or hydrogen and $R_4$ is phenyl which is unsubstituted or mono- or disubstituted by alkoxy, in which process the carboxylic ester of the formula III

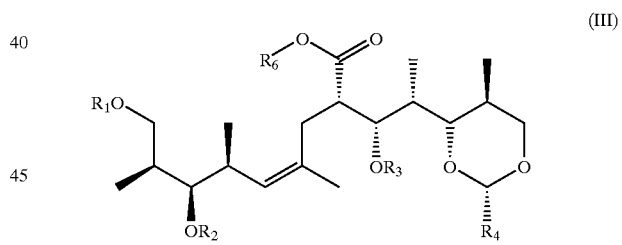

(III)

wherein $R_1$, $R_2$ and $R_3$ are all protecting groups for a hydroxy group which protecting groups can be identical or different, $R_6$ is alkyl or arylalkyl, and $R_4$ has the meaning as defined for the compound of formula I, is first reduced, e.g., by treatment with $LiAlH_4$, the obtained alcohol of the formula IV

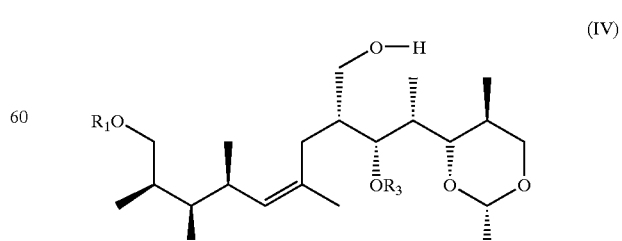

(IV)

wherein $R_1$, $R_2$, $R_3$ and $R_4$ have the meanings as defined above for the compound of formula III, which is further reacted with a compound of formula V $$R_5SO_2Hal \qquad (V)$$

wherein $R_5$ is alkyl or aryl which is unsubstituted or substituted by alkyl, and Hal represent halogen under reaction conditions known as such and the obtained sulfonate of formula II
wherein $R_1$, $R_2$, $R_3$ and $R_4$ have the meanings as defined for the carboxylic ester of formula III and $R_5$ is alkyl or aryl which is unsubstituted or substituted by alkyl, is further reduced, e.g., by treatment with $LiAlH_4$, and, if desired, one, two or all protecting groups $R_1$, $R_2$ and $R_3$ are detached by methods known in the art.

Additionally, the present invention relates to a process for preparing a carboxylic ester of formula III wherein $R_1$ and $R_2$ are protecting groups for a hydroxy group which protecting groups can be identical or different, $R_3$ is hydrogen, $R_4$ is phenyl which is unsubstituted or mono- or disubstituted by alkoxy, and $R_6$ is alkyl or arylalkyl, In which process an allyl halide of the formula VI

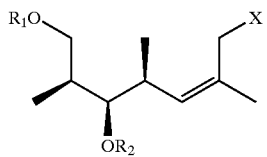

(VI)

wherein $R_1$ and $R_2$ have the meanings as defined for a carboxylic ester of formula III and X is halogen, preferably bromine or iodine, is reacted with a carboxylic ester of formula VII

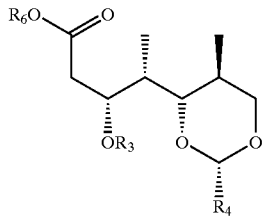

(VII)

wherein $R_3$, $R_4$ and $R_6$ have the meanings as defined for a carboxylic ester of formula III in the presence of a base.

The invention also especially relates to a sulfonate of formula II wherein $R_1$, $R_2$ and $R_3$ are all protecting groups for a hydroxy group which protecting groups can be identical or different, $R_4$ is phenyl which is unsubstituted or mono-or disubstituted by alkoxy, preferably monosubstituted by alkoxy, and $R_5$ is alkyl or aryl which is unsubstituted or substituted by alkyl and to the synthesis of such sulfonate. Preferably in such sulfonate of formula II, $R_1$ and $R_2$ are identical, $R_1$, $R_2$ and $R_3$ are benzyl or silyl protecting groups, and $R_5$ is lower alkyl or phenyl which is substituted, most preferably monosubstituted, by lower alkyl. In a very preferred embodiment, $R_1$ and $R_2$ and $R_3$ are all tert-butyl dimethylsylyl, $R_4$ is phenyl which is unsubstituted or monosubstituted by methoxy and $R_5$ is methyl or phenyl which is monosubstituted by lower alkyl.

Furthermore, the invention especially relates to a carboxylic ester of formula III wherein $R_1$ and $R_2$ are protecting groups for a hydroxy group which protecting groups can be identical or different, $R_3$ is a protecting group for a hydroxy group or hydrogen, $R_4$ is phenyl which is unsubstituted or mono- or disubstituted by alkoxy, and $R_6$ is alkyl or arylalkyl. In a preferred embodiment of the invention, the carboxylic ester of formula III comprises radicals $R_1$ and $R_2$, which are identical, $R_1$, $R_2$ and $R_3$ are silyl protecting groups and $R_6$ is lower alkyl.

Furthermore, the invention especially relates to an alcohol of formula IV wherein $R_1$, $R_2$ and $R_3$ are all protecting groups for a hydroxy group which protecting groups can be identical or different and $R_4$ is phenyl which is unsubstituted or mono- or disubstituted by alkoxy.

Additionally, the present invention relates to a carboxylic ester of formula VII wherein $R_3$ is hydrogen, $R_4$ is phenyl which is unsubstituted or mono- or disubstituted by alkoxy, and $R_6$ is alkyl or arylalkyl.

Furthermore, the invention relates to an oxazolidinone of formula VIII

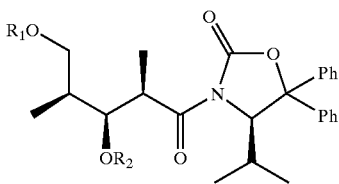

(VIII)

wherein Ph denotes phenyl, and $R_1$ and $R_2$ are independently of each other a silyl protecting group, hydrogen or benzyl which is unsubstituted or mono- or disubstituted by lower alkoxy, or $R_1$ and $R_2$ together represent methyliden substituted by phenyl which phenyl group is mono- or disubstituted by lower alkoxy, and to an oxazolidinone of formula IX

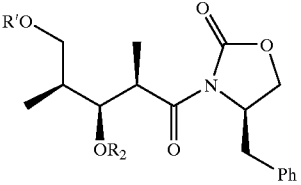

(IX)

wherein Ph denotes phenyl and $R_1$ and $R_2$ are independently of each other a silyl protecting group, hydrogen or benzyl which is unsubstituted or mono- or disubstituted by lower alkoxy under the proviso that one of both radicals $R_1$ and $R_2$ is a silyl protecting group.

Moreover, the invention relates to a δ-valerolactol of the formula X

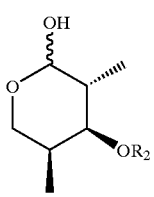

(X)

wherein $R_2$ is a protecting group for a hydroxy group and to an alcohol of the formula XI

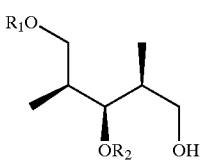

wherein both $R_1$ and $R_2$ represent a silyl protecting group.

Additionally, the invention relates to the use of a sulfonate of formula II, of a carboxylic ester of formula II, an alcohol of formula IV or a carboxylic acid of formula VII, all as defined above, in a process for the manufacture of (+)-discodermolide or discodermolide analogues.

Furthermore, the invention relates to a process for preparing an ether of formula XXVI

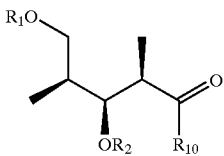

wherein $R_1$ is benzyl which is mono- or disubstituted by alkoxy, $R_2$ represents a protecting group for a hydroxy group or hydrogen and $R_{10}$ is N-oxazolidinyl which is unsubstituted or substituted by alkyl, benzyl or phenyl; $OR_e$ wherein $R_e$ is alkyl or benzyl, or $N(R_a)_2$ wherein $R_a$ is alkyl or benzyl, in which process a compound of formula XXVII,

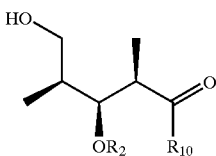

in which the radicals $R_2$ and $R_{10}$ are as defined for the compound of formula XXVI, is reacted with a trichloroacetimidate of formula XVII,

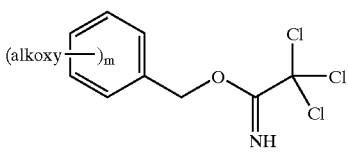

wherein m is 1 or 2 and alkoxy is preferably lower alkoxy, in particular methoxy, in the presence of catalytic amounts of samarium triflate or ytterbium triflate in a suitable solvent, especially dichloromethane, at a temperature between $-15°$ C. and $+15°$ C., preferably between $-5°$ C. and $+5°$ C., in particular at about 0° C., and afterwards, if desired, the protecting group $R_2$ is split off.

Within the present disclosure, the general definitions used hereinbefore and hereinafter preferably have the following meaning, if not indicated otherwise:

The prefix "lower" means that the respective moiety preferably has up to and including a maximum of 7 carbon atoms, more preferably up to 4 carbon atoms.

A protecting group for a hydroxy group as defined herein is a protecting group that can be detached under basic or neutral conditions, i.e. in a medium having a pH≧7, and is especially benzyl which is unsubstituted or mono-or disubstituted by alkoxy, in particular lower alkoxy, preferably methoxy, or, more particular, a silyl protecting group. A silyl protecting group is a group consisting of a silicium atom having a free valence and bearing three groups selected from aryl, alkyl and arylalkyl. A silyl protecting group is in particular a trialkylsilyl- or diaryl-alkylsilyl protecting group, like triethylsilyl, diethyl isopropylsilyl, and, very preferably, tert-butyl dimethylsilyl.

Alkyl is preferably lower alkyl which can be linear or branched and is especially ethyl, n-propyl, isopropyl, n-butyl, isobutyl, sec-butyl or, preferably, methyl or tert-butyl.

Alkoxy is preferably lower alkoxy, e.g. ethoxy or tert-butoxy, and very preferably methoxy.

Aryl is in particular $C_6$–$C_{10}$aryl, especially phenyl or naphthyl.

Arylalkyl is in particular benzyl.

Halogen is preferably fluorine, chlorine, bromine or iodine.

Any reference to other documents or publications within this application means that the respective document or publication is included by reference into the present disclosure.

Substituted alkenes of formula I as defined above are suitable intermediates for the manufacture of (+)-discodermolide and discodermolide analogues.

In particular, a substituted alkene of formula I, wherein all groups $R_1$, $R_2$ and $R_3$ are tert-butyl dimethylsilyl, can be selectively transformed into a compound of formula I, wherein $R_1$ is hydrogen and $R_2$ and $R_3$ are both tert-butyl dimethylsilyl, by treatment of the compound with trifluoroacetic acid in a mixture of tetrahydrofurane and water. Afterwards, the hydrogen atom in the group $R_1$ can be replaced by a 4-methoxybenzyl group by further reacting the compound of formula I with a convenient reagent, e.g., 4-methylchloride or -bromide in the presence of $Ag_2O$ in a suitable solvent like dimethylformamid at ambient temperature. Further suitable reagents and reaction conditions are described by T. W. Greene, "Protective Groups in Organic Synthesis", Wiley, New York 1981, on page 29 and in the references cited there. Very preferably, the hydrogen atom in the group $R_1$ is replaced by a 4-methoxybenzyl group by reacting a substituted alkene of formula I wherein $R_1$ is hydrogen with a compound of formula XVII

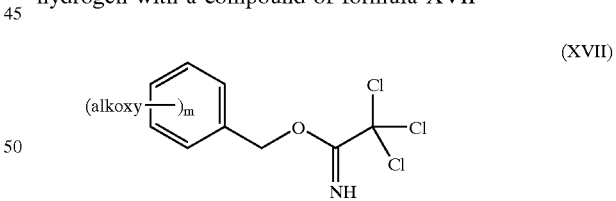

wherein m is 1 in a suitable solvent like dichloromethane in the presence of a suitable catalyst, e.g., samarium triflate or ytterbium triflate.

The suitability of the resulting substituted alkene of formula I, wherein $R_1$ is 4-methoxy-benzyl, $R_2$ and $R_3$ are tert-butyl dimethylsilyl and $R_4$ is 4-methoxyphenyl, for the manufacture of (+)-discodermolide was shown by Amos B. Smith III et al, e.g., in J. Am. Chem. Soc. 2000, 122, 8654–8664, In which publication the transformation of such substituted alkene of formula I (compound "AB" in Scheme 7 on page 8658 and Scheme 9 on page 8659) to (+)-discodermolide is disclosed.

The substituted alkene of formula I, wherein $R_1$, $R_2$ and $R_3$ are independently of each other a protecting group for a hydroxy group or hydrogen and $R_4$ is phenyl which is unsubstituted or mono-or disubstituted by alkoxy, is prepared from a sulfonate of formula II, wherein $R_1$, $R_2$ and $R_3$ are all protecting groups for a hydroxy group which protecting groups can be identical or different, $R_4$ has the meaning as defined for the compound of formula I and $R_5$ is alkyl or aryl which is unsubstituted or substituted by alkyl, which sulfonate is reduced, for example, with $LiAlH_4$, under conditions which are known as such, e.g. by addition of $LiAlH_4$ to a solution of the compound of formula II In a suitable solvent at a temperature between −100 and −25° C., e.g. −78° C. Suitable solvents are, e.g., diethyl ether, diglmne and, in particluar, tetrahydrofuran. The reduction can be accomplished, e.g., alternatively with $NaBH_4$ in a polar aprotic solvent, with $LlEt_3BH$, with $Bu_3SnH$—NaI or with NaI and Zn in 1,2-dimethoxyethane.

The reduction of the carboxylic ester of the formula III wherein $R_1$, $R_2$ and $R_3$ are all protecting groups for a hydroxy group which protecting groups can be identical or different, $R_6$ is alkyl or arylalkyl, and $R_4$ is phenyl which is unsubstituted or mono-or disubstituted by alkoxy, furnishing an alcohol of the formula IV wherein $R_1$ to $R_4$ have the meanings as defined for the compound of formula III, is known as such and can be carried out utilizing reagents like $LiBH_4$, (isobutyl)$_2$AlH, lithium triethylborohydride, $BH_3$—S(methyl)$_2$ in refluxing tetrahydrofurane, triethoxysilane or sodium in ethanol. Preferably the reaction is carried out using $LiAlH_4$ in a suitable solvent like tetrahydrofurane.

The alcohol of the formula IV wherein $R_1$, $R_2$ and $R_3$ are all protecting groups for a hydroxy group which protecting groups can be identical or different, and $R_4$ is phenyl which is unsubstituted or mono- or disubstituted by alkoxy, is reacted with a compound of formula V wherein $R_5$ is alkyl or aryl which is unsubstituted or substituted by alkyl, and Hal represent halogen, to a sulfonate of formula II wherein $R_1$, $R_2$, $R_3$ and $R_4$ have the meanings as defined for the alcohol of formula IV and $R_5$ is alkyl or aryl which is unsubstituted or substituted by alkyl, under conditions known as such. Preferably, the reaction is carried out in the presence of a base, e.g. pyridine, in a suitable inert solvent.

A compound of formula III, wherein $R_1$ and $R_2$ are protecting groups for a hydroxy group which protecting groups can be identical or different, $R_3$ is hydrogen and $R_6$ is alkyl or arylalkyl, and $R_4$ is phenyl which is unsubstituted or mono-or disubstituted by alkoxy, can also be reacted to a compound of formula I wherein $R_1$, $R_2$ and $R_4$ have the same meaning as in the compound of formula III and $R_3$ is a protecting group for a hydroxy group in a one-flask synthesis, i.e. without isolating the intermediates described herein.

Preparation of a Compound of Formula VII

A compound of formula VII, wherein $R_3$ is hydrogen, $R_4$ is phenyl which is unsubstituted or mono-or disubstituted by alkoxy, and $R_6$ is alkyl or arylalkyl is obtained, e.g., by reacting an aldehyde of formula XII

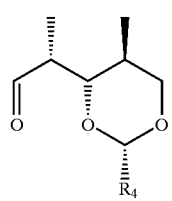

(XII)

wherein $R_4$ is phenyl which is unsubstituted or mono-or disubstituted by alkoxy with a compound of formula XIII, $$CH_3CO_2R_6 \quad (XIII)$$

wherein $R_6$ is alkyl or arylalkyl, in a convenient solvent, in particular, tetrahydrofurane, in the presence of a strong base, preferably lithium diisopropylamide (LDA), and optionally N,N,N',N',N",N"-hexamethylphosphotriamide (HMPTA) and a chiral mediator or catalyst, at a temperature between −100° C. and −0° C., e.g., −78° C.

An aldehyde of formula XII wherein the radical $R_4$ is phenyl which is unsubstituted or mono- or disubstituted by alkoxy is prepared by a conventional oxidation reaction, e.g., by a Swern oxidation, of an alcohol of formula XIV,

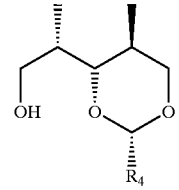

(XIV)

wherein $R_4$ has the meaning as defined for a compound of formula XII. Preferably, oxalyl chloride in a suitable solvent, e.g., dichloromethane, is mixed with dimethylsulfoxide in the same solvent and the alcohol of formula XIV is then added at a temperature between about −50° C. and −100° C., e.g., −78° C. Afterwards, a suitable base, especially diisopropylethylamine, is added at the same temperature.

An alcohol of formula XIV wherein $R_4$ is phenyl which is unsubstituted or mono- or disubstituted by alkoxy is prepared from an acetal of formula VIII wherein $R_1$ and $R_2$ together represent methyliden substituted by phenyl which phenyl group is mono- or disubstituted by alkoxy by reacting the latter compound with $LiAlH_4$ in a suitable solvent, especially tetrahydrofurane, at a temperature between about −50° C. and −100° C., e.g., −78° C.

An acetal of formula VIII wherein $R_1$ and $R_2$ together represent methyliden substituted by phenyl which phenyl group is mono- or disubstituted by alkoxy can be obtained by two different synthetic routes:

(a) An aldehyde of formula XV

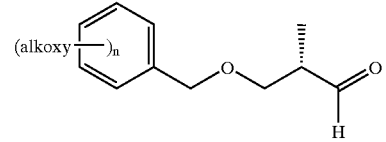

(XV)

wherein n is 1 or 2, is first reacted with a ketone of formula XVI

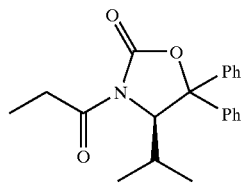

(XVI)

wherein Ph denotes phenyl in a suitable solvent, e.g. dichloromethane in the presence of a more than equimolar amount of dibutylboryltriflate and a base, preferably, diisopropylethylamine, at a temperature between −15° C. and +15° C., e.g. 0° C., to furnish an oxazolidinone of formula VIII,

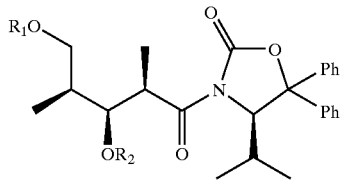

(VIII)

wherein $R_1$ is benzyl which is mono- or disubstituted by alkoxy, and $R_2$ is hydrogen.

Such oxazolidinone of formula VIII is further transformed into a corresponding compound of formula VIII wherein $R_2$ is a protecting group for a hydroxy group which protecting group is not detached by hydrogenolysis, e.g., tert-butyl-dimethylsilyl, by reaction with a reagent capable to introduce such protecting group, e.g., by reaction with tert-butyl-dimethylsilyl-triflate in a suitable solvent like toluene, chloroform or dichloromethane in the presence of a base, e.g. 2,6-lutidine.

Hydrogenolysis of the obtained silyl-protected compound of formula VIII, e.g., by reaction of such compound with hydrogen in the presence of a catalyst like palladium on charcoal using an alcohol as solvent, provides a compound of formula VIII, wherein $R_1$ is hydrogen and $R_2$ is a protecting group for a hydroxy group as defined before.

In an alternative embodiment of the invention a compound of formula VIII, wherein $R_1$ is hydrogen and $R_2$ is a protecting group for a hydroxy group is provided by the following route.

A compound of formula XVI as defined above is first reacted with methacrolein in a suitable solvent, e.g. dichloromethane in the presence of a more than equimolar amount of dibutylboryltriflate and a base, preferably, diisopropylethylamine, at a temperature between −15° C. and −90° C., preferably about −75 to −80° C., to furnish an oxazolidinone of formula XVIII,

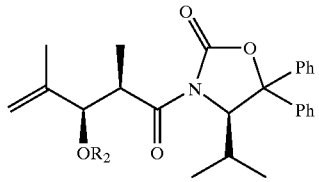

(XVIII)

wherein Ph denotes phenyl and $R_2$ is hydrogen.

Said oxazolidinone of formula XVIII is then further transformed into a corresponding compound of formula XVIII wherein $R_2$ is a protecting group for a hydroxy group, e.g., tert-butyl-dimethylsilyl, by reaction with a reagent capable to introduce such protecting group, e.g., by reaction with tert-butyl-dimethylsilyl-triflate In a suitable solvent like toluene, chloroform or dichloromethane in the presence of a base, e.g. 2,6-lutidine.

Finally, the obtained oxazolidinone of formula XVIII wherein $R_2$ is a protecting group for a hydroxy group is reacted with thexyl borane, or, preferably, 9-BBN (9-borabicyclo[3.3.1]-nonane) in a suitable solvent, e.g. tetrahydrofurane, at a temperature between −5° C. and +35° C. in order to furnish the compound of formula VIII, wherein $R_1$ is hydrogen and $R_2$ is a protecting group for a hydroxy group.

The compound of formula VIII, wherein $R_1$ is hydrogen and $R_2$ is a protecting group for a hydroxy group is then contacted with a trichloroacetimidate of formula XVII

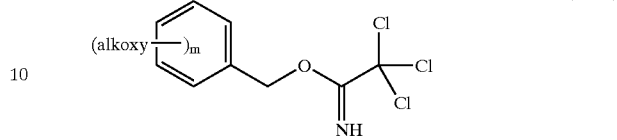

(XVII)

wherein m is 1, 2 or 3, in a suitable solvent like dichloromethane in the presence of a suitable catalyst, e.g., samarium triflate or ytterbium triflate, in order to furnish a compound of formula VIII, wherein $R_1$ is benzyl which is mono- or disubstituted by alkoxy and $R_2$ is a protecting group for a hydroxy group which protecting group is not detached by hydrogenolysis.

Such compound of formula VIII is then further reacted with a reagent capable of detaching the protecting group $R_2$ under conditions leaving the group $R_1$ unchanged, which conditions are known as such. For example, if $R_2$ is tert-butyl-dimethylsilyl, the reagent capable of detaching such group can be aqueous hydrogenfluoride to be combined with the compound of formula VII in acetonitrile or another suitable lower alkyl cyanide. The reaction provides a compound of formula VII wherein $R_1$ is benzyl which is mono- or disubstituted by alkoxy and $R_2$ is hydrogen.

The desired acetal of formula VIII wherein $R_1$ and $R_2$ together represent methyliden substituted by phenyl which phenyl group is mono- or disubstituted by alkoxy is obtained by treating such compound of formula VII wherein $R_1$ is benzyl which is mono-or disubstituted by alkoxy and $R_2$ is hydrogen with DDQ (2,3-dichloro-5,6-dicyano-1,4-benzoquinone) which reaction can be carried out in a suitable solvent like dichloromethane at a temperature between −10° C. and +10° C., preferably at about 0° C.

(b) The oxazolidinone of formula XVIII, wherein Ph denotes phenyl and $R_2$ is hydrogen, obtained as described above, can also be reacted with thexyl borane, or, preferably, 9-BBN (9-borabicyclo[3.3.1]nonane) in a suitable solvent, e.g. tetrahydrofurane, at a temperature between −5° C. and +35° C. without prior protection of the hydroxy group present in the compound. The reaction product is a compound of formula VIII wherein $R_1$ and $R_2$ are both hydrogen. Such product can be further reacted in a suitable solvent, like dichloromethane, at a temperature, e.g., between 15° C. and 30° C. in the presence of a suitable acid like toluene sulphonic acid, camphor sulfonic acid or, preferably, Amberlyst 15 with a compound of formula XIXa

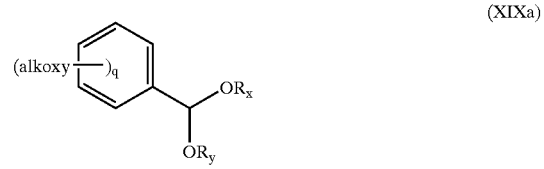

(XIXa)

wherein q is 0, 1 or 2, and $R_x$ and $R_y$ are lower alkyl furnishing the desired acetal of formula VIII wherein $R_1$ and $R_2$ together represent methyliden substituted by phenyl which is mono- or disubstituted by alkoxy.

Alternatively, a compound of formula VIII wherein $R_1$ and $R_2$ are both hydrogen can also be transferred into an acetal of formula VIII wherein $R_1$ and $R_2$ together represent methyliden substituted by phenyl which is mono- or disubstituted by alkoxy by reaction with a compound of formula XIXb

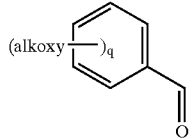

(XIXb)

wherein q is 0, 1 or 2, in a suitable solvent, like dichloromethane or benzene, under reaction conditions known as such, especially at the reflux temperature of the solvent optionally in the presence of a reagent that reacts with the water that is obtained in the course of the reaction, like dicyclohexyl carbodilmide.

A further alternative for obtaining an acetal of formula VIII wherein $R_1$ and $R_2$ together represent methyliden substituted by phenyl which is mono-or disubstituted by alkoxy starting from a compound of formula VIII wherein $R_1$ and $R_2$ are both hydrogen constitutes the reaction of the latter compound with a compound of formula XIXc

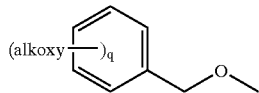

(XIXc)

wherein q is 0, 1 or 2 and 2,3-dichloro-5,6-dicyano-1,4-benzoquinone (DDQ) in a suitable solvent, e.g. dichloromethane, under reaction conditions known as such.

The δ-valerolactol of the formula X and the δ-valerolacton of the formula XX

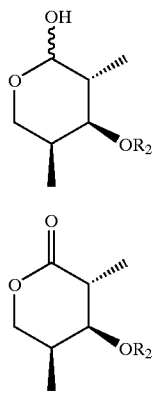

(X)

(XX)

wherein in both cases $R_2$ is a protecting group for a hydroxy group are suitable starting materials for the synthesis of the compounds of formula VI and VII. For example, the compound of formula (XX) wherein $R_2$ is a protecting group for a hydroxy group can be reacted with LiOH and a reagent capable of introducing a protecting group for a hydroxy group $R_2$ in a suitable solvent to provide a compound of formula XXV

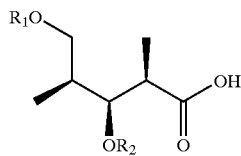

(XXV)

wherein $R_1$ and $R_2$ are independently of each other a protecting group for a hydroxy group. Such compound can then be reduced with reagents known as such, e.g. $NaBH_4$ together with $AlCl_3$ in diglyme, $BH_3$ in tetrahydrofurane, $LiAlH(O-methyl)_3$ in tetrahydrofurane, $AlH_3$ in diethylether, $LiAlH_4$ in diethylether or diisobutyl aluminium hydride in tetrahydrofurane, in all cases under conditions known such, to furnish a compound of formula XI

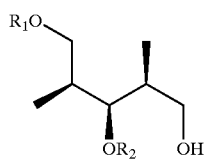

(XI)

wherein $R_1$ and $R_2$ have the meanings as defined for the compound of formula XXV.

Said lactol of formula X is obtained by reacting said lacton of formula XX with DIBAH (diisobutylaluminium hydride) in a suitable solvent, like tetrahydrofurane, at a temperature between about −85 to −70° C.

The lacton of formula XX wherein $R_2$ is a protecting group for a hydroxy group is the product of the reaction of a compound of formula VIII wherein $R_1$ is hydrogen and $R_2$ is a protecting group for a hydroxy group with a catalytic amount of a potassium alcoholate, e.g. potassium tert-butanolate, in a suitable solvent, e.g. tetrahydrofurane, at a temperature between about −10° C. and +10° C., e.g. 0° C.

Alternatively, the lacton of formula XX wherein $R_2$ is a protecting group for a hydroxy group can be prepared by the following synthetic route:

An aldehyde of formula XV wherein n is 1 or 2, is first reacted with a ketone of formula XXI

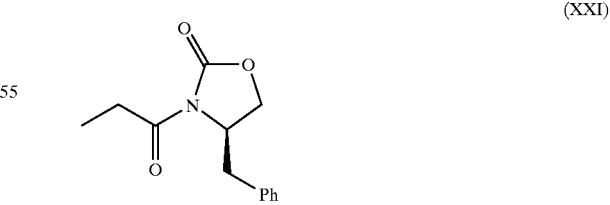

(XXI)

wherein Ph denotes phenyl, in a suitable solvent, e.g. dichloromethane in the presence of a more than equimolar amount of dibutylboryltriflate and a base, preferably, diisopropyl-ethylamine, at a temperature between −15° C. and +15° C., e.g. 0° C., to furnish an oxazolidinone of formula IX,

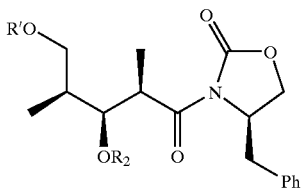

wherein Ph denotes phenyl and R' is benzyl which is unsubstituted or mono-or disubstituted by alkoxy and $R_2$ is hydrogen.

Such oxazolidinone of formula IX is then further transformed into a corresponding compound of formula IX wherein $R_2$ is a protecting group for a hydroxy group which protecting group is not detached by hydrogenolysis, e.g., tert-butyl-dimethylsilyl, by reaction with a reagent capable to introduce such protecting group, e.g., by reaction with tert-butyl-dimethylsilyl-triflate in a suitable solvent like toluene, chloroform or dichloromethane in the presence of a base, e.g. 2,6-lutidine.

Hydrogenolysis of the obtained protected compound of formula IX, e.g., by reaction of such compound with hydrogen in the presence of a catalyst like palladium on charcoal using an alcohol as solvent, provides a compound of formula IX, wherein $R_1$ is hydrogen and $R_2$ is a protecting group for a hydroxy group as defined before.

Such compound of formula IX, wherein $R_1$ is hydrogen and $R_2$ is a protecting group for a hydroxy group which protecting group is not detached by hydrogenolysis provides the desired lacton XX by reaction with $H_2O_2$ in a mixture of a suitable solvent, e.g. tetrahydrofurane, with water in the presence of LiOH at a temperature between $-15°$ C. and $+15°$ C., e.g. $0°$ C.

Preparation of the Allyl Halide of Formula VI

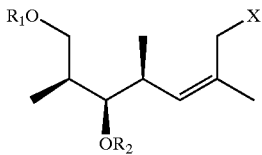

wherein $R_1$ and $R_2$ are protecting groups for a hydroxy group which protecting groups can be identical or different and X is halogen is obtained by the following reaction steps:

The oxazolidinone of formula VIII, wherein Ph denotes phenyl and wherein $R_1$ and $R_2$ are both hydrogen, obtained as described above, is transformed into a corresponding compound of formula VIII wherein $R_1$ and $R_2$ are both protecting groups for a hydroxy group which protecting groups are not detachable under the reaction conditions of the following reaction steps providing the desired compound of formula VI, preferably a silyl protecting group for a hydroxy group, e.g., tert-butyl-dimethylsilyl, by reaction with a reagent capable to introduce such protecting groups, e.g., by reaction with tert-butyl-dimethylsilyl-triflate in a suitable solvent like toluene, chloroform or dichloromethane in the presence of a base, e.g. 2,6-lutidine.

The latter compound of formula VIII is then reacted with a suitable reduction reagent, preferably $LiBH_4$, in a suitable solvent, e.g. a mixture of tetrahydrofuranee and water, at a temperature between about $-5°$ C. and $+30°$ C. to provide an alcohol of the formula XI

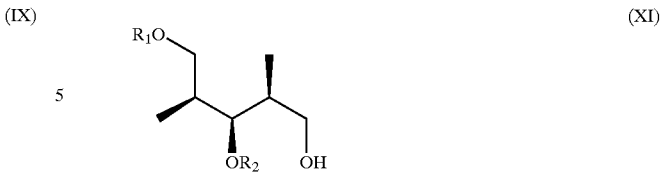

wherein both $R_1$ and $R_2$ represent a protecting group for a hydroxy group which protecting group is not detachable under the reaction conditions of the following reaction steps providing the desired compound of formula VI, preferably a silyl protecting group.

Such alcohol of formula XI is then oxidized by a suitable reagent, preferably via Swern oxidation, to the corresponding aldehyde of formula XXII

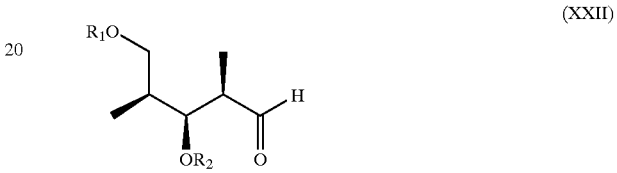

wherein $R_1$ and $R_2$ are as defined above for a compound of formula XI. Wittig olefination with a phosphonate of formula XXIII

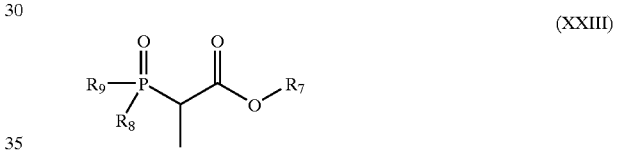

wherein $R_7$ is alkyl or arylalkyl and $R_8$ and $R_9$ are independently of each other alkyl which is unsubstituted or substituted by halogen, preferably fluorine, provides an α,β-unsaturated carboxylic acid ester of formula XXIV

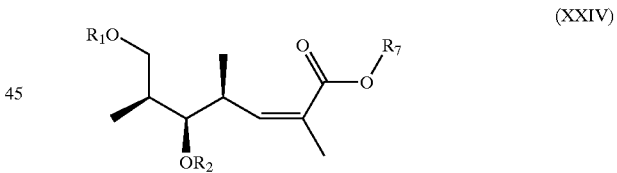

wherein $R_1$ and $R_2$ are as defined above for a compound of formula XI and $R_7$ is alkyl or arylalkyl. The reaction is preferably accomplished in tetrahydrofurane in the presence of the base potassium hexamethyldisilazane and 18-crown-6.

Said compound of formula XXIV is further reacted with DIBAH or another reagent, especially a reagent disclosed herein, capable of transforming a carboxylic ester into an alcohol, in a suitable solvent, for example, in the case of DIBAH in dichloromethane, to furnish an allylic alcohol of formula VI wherein $R_1$ and $R_2$ are protecting groups for a hydroxy group which protecting groups can be identical or different and X is hydroxy.

Finally, the allylic alcohol of formula VI is transformed into the desired allylic halide of formula VI, preferably an allylic iodide by reaction with iodine in the presence of triphenylphosphine and imidazole in a suitable solvent, e.g., a mixture of diethylether and a lower alkyl nitrile.

The skilled person will understand that the reaction conditions given above can be replaced by analogous reaction conditions that are in principle known in the art. Furthermore, a person skilled in the art will be aware of suitable protecting groups of hydroxy that can replace the protecting groups used in the specific Examples below and how to attach such groups to free hydroxy groups present in the compounds described hereinbefore and hereinafter, especially in a compound of formula I, IV, VIII or IX, and how to detach such groups, if desired. In addition, the skilled person will be able to select the appropriate specific reaction conditions for the reaction steps given hereinbelow and hereinafter where reactions are described generally herein. All those reaction conditions are included in the scope of the present invention.

The protection of hydroxy groups by protecting groups, the protecting groups themselves, and their cleavage reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Melenhofer), Academic Press, London and New York 1981, In "Methoden der organischen Chemie" (Methods of organic chemistry), Houben Weyl, 4th edition, Volume 15/I, Georg Thieme Verlag, Stuttgart 1974, in H. -D. Jakubke and H. Jescheit, "Aminosauren, Peptide, Proteine" (Amino acids, peptides, proteins), Verlag Chemie, Weinheim, Deerfield Beach, and Basel 1982, and in Jochen Lehmann, "Chemie der Kohlenhydrate: Monosaccharide und Derivate" (*Chemistry of carbohydrates: monosaccharides and derivatives*), Georg Thieme Verlag, Stuttgart 1974.

The following examples are for purposes of illustration only and are not intended to limit in any way the scope of the instant invention. Starting materials can be purchased or prepared by the methods mentioned hereinafter.

| Abbreviations: | |
|---|---|
| aqu. | aqueous |
| 9-BBN | 9-borabicyclo[3.3.1]nonane |
| brine | saturated sodium chloride solution |
| bu | butyl |
| DIBAH | diisobutylaluminium hydride |
| DDQ | 2,3-dichloro-5,6-dicyano-1,4-benzoquinone |
| DMSO | dimethyl sulfoxide |
| Et | ethyl |
| EtOAc | ethyl acetate |
| FC | flash-chromatography |
| h | hour(s) |
| HMPA | N,N,N',N',N'',N''-hexamethylphosphotriamide |
| HRMS | high resolution mass spectrometry |
| K | Kelvin |
| KHMDS | potassium hexamethyldisilazane |
| min | minute(s) |
| m.p. | melting point |
| Me | methyl |
| MS | mass spectrometry |
| MS(EI) | electrospray ionisation mass spectrum |
| Ph | phenyl |
| PTLC | preparative thin layer chromatography |
| RT | room temperature |
| sat. | saturated |
| TBDMS | tert-butyl-dimethylsilyl |
| TBME | tert-butyl methyl ether |
| TBSOTf | tert-butyl-dimethylsilyl-trifluoromethanesulfonate |
| Tf | trifluoromethanesulfonate |
| THF | tetrahydrofurane |

| Abbreviations for th NMR spectra data | |
|---|---|
| b | broad |
| d | doublet |
| J | coupling constant |
| m | multiplet |
| q | quartet |
| s | singlet |
| t | triplet |
| ppm | parts per million |

EXAMPLE 1

(4R)-4-Benzyl-(N)-[(2R, 3S, 4S)-5-(4-methoxybenzyloxy)-2,4-dimethyl-3-(tert-butyl-dimethylsilyloxy)-valeryl]-oxazolidin-2-one The alcohol from stage 1.1 (1.36 g, 3.1 mmol) is dissolved in 10 mL of $CH_2Cl_2$ under an atmosphere of argon and cooled to 0° C. 2,6-Lutidine (0.49 mL, 4.0 mmol, 1.3 eq.) is added followed by dropwise addition of TBSOTf (0.78 mL, 3.4 mmol, 1.1 eq.). The reaction mixture is stirred for 30 min, poured onto ice water and extracted with hexane. The organic layer is washed with 1N HCl, sat. aqu. $NaHCO_3$ and sat. aqu. NaCl, then dried over $MgSO_4$ and concentrated in vacuo to give the title compound as a colorless oil.

Stage 1.1: A solution of (R)-4-benzyl-(N)-propionyloxazolidin-2-one (Aldrich, 336 mg, 1.44 mmol) in 3.0 mL dichloromethane is treated with a 1.0 M solution (1.6 mL, 1.6 mmol) of $Bu_2BOTf$ at 0° C. under an atmosphere of argon. To the resulting brown-red mixture 0.30 mL (1.7 mmol) of diisoproylethylamine is added to give a colorless, clear solution, which is stirred a 0° C. for 1 h. Then a solution of (S)-3-(4-methoxybenzyloxy)-2-methyl-propionaldehyde (Aldrich, 300 mg, 1.44 mmol) dissolved in 1.5 mL of $CH_2Cl_2$ is added slowly at −78° C. The reaction mixture is stirred at this temperature for 60 min and at 0° C. for 45 min. Phosphate buffer pH 7.0 is added followed by extraction (3 times) with TBME. The combined organic layers are washed with sat. aqu. NaCl solution, dried over $MgSO_4$ and concentrated in vacuo. The residue is redissolved in 5 mL of methanol and treated with 2 mL of aqu. $H_2O_2$ (30%) at 0° C. After stirring for 1 hour the volatiles are removed in vacuo and the aqueous phase is extracted with TBME (3 times). The combined organic layers are washed with sat. $NaHCO_3$ and brine, dried over $MgSO_4$, and concentrated in vacuo. After chromatographic purification ($SiO_2$, heptane/ethylacetate 2:1) the desired alcohol is obtained as a colorless oil.

EXAMPLE 2

(4R)-4-Benzyl-(N)-[(2R, 3S, 4S)-5-hydroxy-2,4-dimethyl-3-(tert-butyl-dimethylsilyloxy)-valeryl]-oxazolidin-2-one A solution of 132 mg (0.24 mmol) of the TBDMS ether from Example 1 in 3.0 mL of methanol is hydrogenated in the presence of a catalytic amount of Pd/C under 1 bar of hydrogen atmosphere for 6 h at 23° C. After filtration of the reaction mixture through a pad of celiflock which is washed 3 times with ethylacetate, concentration in vacuo and FC($SiO_2$, hexanes/EtOAc 1:1), the title compound is obtained as a colorless oil. $^1$H-NMR ($CDCl_3$, 300 MHz, 300K) δ 7.32–7.05 (m, 5H), 4.62–4.52 (m, 1H), 4.12 (d, J=6.0 Hz, 1H), 4.12–4.0 (m, 2H), 3.50 (dd, J=12.0, 5.3 Hz, 1H), 3.42 (dd, J=12.0, 6.8 Hz, 1H), 3.19 (dd, J=13.5, 3.7 Hz, 1H), 2.70 (dd, J=13.5, 9.0 Hz, 1H), 1.9–1.85 (m, 1H), 1.65–1.45 (br m, 1H), 1.20 (d, J=8.3 Hz, 3H), 0.92 (d, J=7.5 Hz, 3H), 0.88 (s, 9H), 0.05 (s, 3H), 0.00 (s, 3H). MS (EI) m/Z 458 (100, [M+Na]$^+$).

EXAMPLE 3

(1RS, 2R, 3S, 4S)-5-Hydroxy-2,4-dimethyl-3-tert-butyl-dimethylsilyloxy-δ-valerolactol The lactone of stage 3.1 (1.00 g, 3.87 mmol) is dissolved in 40 mL of toluene and 3.10 mL (4.65 mmol) of DIBAH (1.5 M in toluene) is added over 10 min at −78° C. After 30 min at −78° C., the reaction mixture is quenched by addition of 2 mL of MeOH. The resulting mixture is poured on aqu. sat. NH$_4$Cl and the two layers are separated. The aqu. layer is extracted (3 times) with EtOAc. The combined organic phases are washed successively with 10% aqu. H$_2$SO$_4$, sat. aqu. NaHCO$_3$ and sat. aqu. NaCl, dried over MgSO$_4$ and concentrated in vacuo to give the title compound as a colorless oil. $^1$H-NMR (CDCl$_3$, 300 MHz, 300K, mixture of anomers, ratio=4.2:1.0) major anomer: δ 4.68 (br s, 1H); 3.72 (dd, J=11.2, 0.8 Hz, 1H); 3.62 (br m, 1H), 3.32 (dd, J=11.2, 5.6 Hz, 1H); 2.02–1.85 (two m, 2H), 0.93 (d, J=7.1 Hz, 3H), 0.87 (s, 9H), 0.75 (d, J=7.5 Hz, 3H), 0.04 (s, 3H), 0.01 (s, 3H); minor anomer: δ 5.00 (d, J=1.9 Hz, 1H), 3.80–3.67 (m, 1H, obscured by one signal from the major anomer), 3.43 (dd, J=11.3, 7.1 Hz, 1H), 2.05–1.80 (two m, 2H), 0.90 (d, J=7.3 Hz, 3H), 0.84 (s, 9H), 0.82 (d, J=7.5 Hz, 3H), 0.00 (s, 3H), ?0.3 (s, 3H); MS (EI) m/z244 (7, [M−O]$^+$), 204 (55, [M−C(CH$_3$)$_3$]$^+$), 145 (100, [M−Si(CH$_3$)$_2$(CH$_3$)$_3$]$^+$).

Stag 3.1: A solution of the alcohol from Example 2 (43 mg, 0.1 mmol) in 1.5 mL of THF/H$_2$O (3:1) is treated with 40 μl (0.4 mmol, 4.0 eq.) of H$_2$O$_2$ (30%) followed by 8 mg (0.2 mmol, 2.0 eq.) of LiOH monohydrate at 0° C. After stirring for 40 min, 0.3 mL of a 1.5 M aqu. solution of Na$_2$SO$_3$ is added. The reaction is quenched with sat. aqu. NaHCO$_3$ and extracted with TBME. The ether layer is washed with sat. aqu. NaHCO$_3$ solution twice. The combined aqu. extracts are acidified (pH 3) with 1 N HCl and extracted with ethylacetate (3 times). The organic layers are combined, dried over MgSO$_4$ and concentrated in vacuo to give the desired lactone as a colorless crude oil containing some oxazolidinone as the major impurity. $^1$H-NMR DMSO-d$^6$, 400 MHz, 300K) δ 4.20 (dd, J=11.5, 4.0 Hz, 1H), 4.07 (dd, J=11.5, 8.4 Hz, 1H), 3.83 (dd, J=5.3, 2.8 Hz, 1H), 2.47 (qd, J=7.8, 5.3 Hz, 1H), 2.28–2.15 (m, 1H), 1.20 (d, J=7.8 Hz, 3H), 0.90 (d, J=7.1 Hz, 3H), 0.88 (s, 9H), 0.09 (s, 3H), 0.08 (s, 3H). MS (EI) m/z 539 (30, [M+2 Na]$^+$), 322 (55, [M+CH$_3$CN]$^+$).

EXAMPLE 4

(4R)-4-Isopropyl-5,5-diphenyl-(N)-[(2R, 3S, 4S)-5-hydroxy-2,4-dimethyl-3-(tert-butyl-dimethylsilyloxy)-valeryl]-oxazolidin-2-one To a solution of 7.67 g (14.7 mmol) of the TBDMS ether of stage 4.2 in 60 mL of THF at 0° C. under an atmosphere of argon is added 3.59 g (29.4 mmol) of 9-BBN in 50 mL of THF. After 15 min at 0° C. the reaction mixture is warmed to ambient temperature with stirring for 5 h. The mixture is recooled to 0° C. and quenched with 19.4 mL each of 1:1 (v/v) EtOH/THF, aqu. pH 7 phosphate buffer, and 35% aqu. hydrogen peroxide. After 30 min, the solution is again warmed to ambient temperature and stirred for 15 h. Heptane (150 mL) and 20% aqu. NaHSO$_3$ (120 mL) are added and the aqu. layers are extracted with heptane (2×100 mL). The combined organic layers are washed with sat. aqu. NaCl (1×100 mL), dried over MgSO$_4$, filtered, and concentrated in vacuo. Purification by FC (SiO$_2$, hexane/AcOEt 4:1) gives the title compound as a colorless oil which crystallizes upon conservation at 4° C. $^1$H-NMR (CDCl$_3$, 300 MHz, 300K) δ 7.55–7.15 (4 m, 10H), 5.27 (d, J=3.5 Hz, 1H), 3.95 (dd, J=9.4, 2.5 Hz, 1H), 3.76 (qd, J=9.4, 6.9 Hz, 1H), 2.91 (dd, J=12.0, 4.9 Hz, 1H), 2.49 (dd, J=12.0, 7.5 Hz, 1H), 1.79 (heptuplet, J=6.8, 3.5 Hz, 1H), 1.72–1.65 (br s, 1H), 1.33–18 (m, 1H), 1.23 (d, J=6.9 Hz, 3H), 0.83, (d, J=6.8 Hz, 3H), 0.81 (s, 9H), 0.72 (d, J=6.8 Hz, 3H), 0.58 (d, J=7.1 Hz, 3H), 0.00 (s, 6H).

The title compound is converted to the lactone of stage 3.1 using the following procedure:

The title compound (2.08 g, 3.85 mmol) is dissolved in 40 mL of THF and a solution of t-BuOK (1.5 M in THF, 77 μL, 77 μMol) is added at 0° C. under an atmosphere of argon. The clear, colorless solution is allowed to stir for 1 h and to warm up to 23° C. A white precipitate is formed. The reaction mixture is diluted with 50 mL of hexane and is filtered. The residue is washed with aqu. sat. NaCl. The filtrate is collected and the two layers separated. The organic layer is dried over MgSO$_4$ and partially concentrated in vacuo. A white precipitate is formed during the concentration. The mixture is filtered and the residue is washed with 5 mL of hexane. The filtrate is collected and concentrated in vacuo to give the pure lactone of stage 3.1 as a colorless oil which solidified upon conservation at 4° C. providing a solid having a m.p. of 53–54° C.

Stage 4.1: A solution of 14.9 mL (87 mmol, 1.45 eq.) of diisoproylethylamine in 30 mL of CH$_2$Cl$_2$ under an atmosphere of argon is treated sequentially at −5° C. over 10 min with a 1.0 M solution (78 mL, 78 mmol, 1.3 eq.) of Bu$_2$BOTf in CH$_2$Cl$_2$ and at −78° C. over 15 min with a solution of (R)-4-isopropyl-5,5-diphenylpropionyloxazolidin-2-one (20.2 g, 60 mmol; prepared according to T. Hintermann, D. Seebach, Helv. Chim. Acta 1998, 81, 2093) in 60 mL of CH$_2$Cl$_2$ to give a clear orange solution. After 10 min at −78° C., the solution is warmed to 0° C. with stirring for 1 h, after which it is recooled to −78° C. again. A solution of methacrolein (14.8 mL, 180 mmol, 3 eq.) dissolved in 20 ml of CH$_2$Cl$_2$ is then added slowly over a period of 30 min. After 30 further min stirring, the reaction mixture is warmed to 0° C. with stirring for 1 h. Phosphate buffer pH 7.0 (60 mL), MeOH (180 mL) and MeOH/35% H$_2$O$_2$ (2:1 v/v, 180 mL) are added sequentially at 0° C. After stirring for 3 h at ambient temperature, the mixture is recooled to 0° C. and treated with 40% aqu. NaHSO$_3$ (80 mL). The volatiles are removed in vacuo and the aqu. phase is extracted with toluene (3×200 mL). The combined organic layers are washed with 1N HCL (60 mL), sat. aqu. NaHCO$_3$ (60 mL) and sat. aqu. NaCl (60 mL) solutions, dried over MgSO$_4$, filtered, and concentrated in vacuo to give 28.6 g of the desired alcohol as slightly yellowish crude solid residue, a sample of which is purified by FC (SiO$_2$, hexane/AcOEt 3:1) to afford the pure alcohol as white crystals with a m.p. of 99.5–100.0° C.

Stage 4.2: The crude alcohol of stage 4.1 (13.9 g) is dissolved in 50 mL of CH$_2$Cl$_2$ under argon and cooled to 0° C. 2,6-Lutidine (4.9 mL, 42 mmol) is added followed by dropwise addition over 10 min of TBSOTf (7.1 mL, 31 mmol). The reaction mixture is stirred for 30 min at 0° C., after which 100 mL of hexane and 45 mL of 1N HCL are added sequentially. The aqu. layer is extracted (2 times) with hexane. The combined organic layers are washed with 1N HCl (2 times), sat. aqu. NaHCO$_3$ and sat. aqu. NaCl, then dried over MgSO$_4$ and concentrated in vacuo to give 17.7 g of the crude product as yellow crystals. After recrystallization from 20 mL of hexane with addition of seed crystals, the desired TBDMS ether is obtained as slightly yellowish crystals with a m.p. of 116° C.

EXAMPLE 5

(4R)-4-Isopropyl-5,5-diphenyl-(N)-[(2R, 3S, 4S)-5-hydroxy-2,4-dimethyl-3-(tert-butyl-dimethylsilyloxy)-valeryl]-oxazolidin-2-one A solution of 110 mg (0.17 mmol) of the TBDMS ether of stage 5.2 in 3.0 mL MeOH is hydrogenated in the presence of a catalytic amount of Pd/C under 1 bar of hydrogen atmosphere for 5 h at 23° C. After filtration of the reaction mixture through a pad of cellflock which is washed 3 times with MeOH, concentration in vacuo and FC (SiO$_2$, hexane/EtOAc 5:1) the title compound is obtained as a white solid (physical data see Example 4.

Stage 5.1: A solution of (R)-4-isopropyl-5,5-diphenylpropionyloxazolidin-2-one (see stage 4.1; 1.00 g, 2.96 mmol) in 7.5 mL of dichloromethane is treated with a 1.0 M solution (3.55 mL, 3.55 mmol) of Bu$_2$BOTf at 0° C. under an atmosphere of argon. To the resulting brown-red mixture 0.66 mL (3.85 mmol) of diisoproylethylamine is added to give a colorless, clear solution, which is stirred a 0° C. for 1 h. Then a solution of (S)-3-(4-methoxybenzyloxy)-2-methyl-propionaldehyde (Aldrich, 616 mg, 2.96 mmol) dissolved in 1.0 ml of CH$_2$Cl$_2$ is added slowly at −78° C. The reaction mixture is stirred at this temperature for 60 min and at 0° C. for 60 min. Phosphate buffer pH 7.0 (3.0 mL), MeOH (8.9 mL) and MeOH/30% H$_2$O$_2$ (2:1 v/v, 8.9 mL) are added sequentially at 0° C. After stirring for 1 h at RT, the volatiles are removed in vacuo and the aqu. phase is extracted with TBME (3 times). The combined organic layers are washed with 1N HCL, sat. aqu. NaHCO$_3$ and sat. aqu. NaCl solutions, dried over MgSO$_4$ and concentrated in vacuo. After chromatographic purification (SiO$_2$, heptane/EtOAc 4:1) the desired alcohol is obtained as a colorless oil.

Stage 5.2: The alcohol from stage 5.1 (96 mg, 0.18 mmol) is dissolved in 5 mL of CH$_2$Cl$_2$ under argon and cooled to 0° C. 2,6-Lutidine (31 μL, 0.27 mmol) is added followed by dropwise addition of TBSOTf (50 μL, 0.22 mmol). The reaction mixture is stirred for 45 min at 0° C., poured onto ice water and extracted with TBME (3 times). The combined organic layers are washed with 1N HCl, sat. aqu. NaHCO$_3$ and sat. aqu. NaCl, then dried over MgSO$_4$ and concentrated in vacuo to give the desired product as a colorless oil.

EXAMPLE 6

(4R)-4-Isopropyl-5,5-diphenyl-(N)-[(2R, 3S, 4S)-3,5-dihydroxy-2,4-dimethylvaleryl]-oxazolidin-2-on To a solution of 10.2 g (25.0 mmol) of the allylic alcohol from stage 4.1 in 100 mL of THF at 0° C. under an atmosphere of argon, a solution of 9-BBN (7.56 g, 62.0 mmol, 2.5 eq.) in 130 mL of THF is added over a period of 30 min. After 10 min at 0° C. the reaction mixture is warmed to ambient temperature with stirring for 6.5 h. The mixture is recooled to −15° C. and quenched with 78 mL each of 1:1 (v/v) EtOH/THF, aqu. pH 7 phosphate buffer, and 35% aqu. hydrogen peroxide. After 30 min, the solution is again warmed to ambient temperature and stirred for 15 h. A 40% aqu. solution of NaHSO$_3$ (210 g) and heptane (200 mL) are added sequentially and the aqu. layers are extracted with heptane (2×150 mL). The combined organic layer is washed with 0.2 N NaOH (2×100 mL), sat. aqu. NH$_4$Cl (1×100 mL), and sat. aqu. NaCl (1×100 mL), dried over MgSO$_4$, filtered, and concentrated in vacuo. Purification by FC (SiO$_2$, hexane/AcOEt 1:1) gives 7.38 g of the title compound as a colorless oil which crystallizes upon conservation at 4° C. providing a solid with a m.p. of 103–104° C.

EXAMPLE 7

(4R)-4-Isopropyl-5,5-diphenyl-(N)-[(2R, 3S, 4S)-3,5-bis(tert-butyl-dimethylsilyloxy)-2,4-dimethyl-valeryl]-oxazolidin-2-one The alcohol of Example 6 (1.10 g, 2.04 mmol) is dissolved in 20 mL of CH$_2$Cl$_2$ under an atmosphere of argon and cooled to 0° C. 2,6-Lutidine (0.28 mL, 2.45 mmol, 1.20 eq.) is added followed by dropwise addition of TBSOTf (0.49 mL, 2.14 mmol, 1.05 eq.). The reaction mixture is stirred for 60 min, poured onto 1 N HCl and extracted with heptane (3 times). The organic layer is washed with sat. aqu. NaHCO$_3$ and sat. aqu. NaCl, then dried over MgSO$_4$ and concentrated in vacuo to give the title compound as a colorless oil which crystallizes upon conservation at 4° C. providing a solid with a m.p. of 104–105° C.

EXAMPLE 8

(2S, 3S, 4S)-3,5-Bis(tert-butyl-dimethylsilyloxy)-2,4-dimethyl-pentan-1-ol

A 2.0 M solution of LiBH$_4$ (6.55 mL, 13.10 mmol) in THF is added to a solution of the bis-TBDMS ether of Example 7 (5.36 g, 8.19 mmol) in 130 mL of diethylether and 234 μL (13.02 mmol) of water at 0° C. over a period of 10 min. The mixture is allowed to warm to ambient temperature over night. The chiral auxiliary forms a white crystalline precipitate. Another 73 μL (4.06 mmol) water and 2.05 mL (4.09 mmol) of a 2 M LiBH$_4$ solution are added at 23° C. After additional 6.5 h reaction time further 73 μL (4.06 mmol) water and 2.05 mL (4.09 mmol) of a 2 M LiBH$_4$ solution are added at 23° C. and the resulting mixture is stirred over night. The reaction is quenched by adding 200 mL of 1 N NaOH followed by the addition of 400 mL ethylacetate. The phases are separated and the aqu. layer is extracted twice with 150 mL ethylacetate. The combined organic phases are washed with brine (250 mL), dried over MgSO$_4$ and concentrated in vacuo. The residue is suspended in 80 mL heptane, stirred at 0° C. for 1.5 h and filtered. The obtained cake is washed with cold heptane (75 mL) and dried at 50° C. in vacuo to give recycled auxiliary. The combined filtrates are concentrated to provide the crude title compound as a colorless oil.

cis-(4S, 5R, 6S)-5,7-Bis(tert-butyl-dimethylsilyloxy)-2,4,6-trimethyl-hept-2-en-1-yliodid can be obtained from the title compound by the following procedure:

Stage 8.1: A solution of 0.455 mL (5.30 mmol) oxalylchloride in 20 mL CH$_2$Cl$_2$ is treated with a solution of 0.75 mL (10.6 mmol) DMSO in 1.0 mL CH$_2$Cl$_2$ at −78° C. After 15 min a solution of the title compound (1.0 g, 2.65 mmol) in 8 mL CH$_2$Cl$_2$ is added dropwise over a period of 30 min. Et$_3$N (2.3 mL, 15.9 mmol) is added over 12 min and the reaction mixture is allowed to warm to room temperature. After additional stirring for 30 min 40 mL TBME and 50 mL of a sat. NH$_4$Cl solution are added. The aqu. layer is separated and extracted twice with 30 mL TBME. The combined organic layers are washed with 50 mL brine, dried over MgSO$_4$ and concentrated under reduced pressure. The residual oil is purified by FC (heptane/ethylacetate 100:1.5)

to give the desired aldehyde as a colorless oil. $^1$H-NMR (CDCl$_3$, 300 MHz, 300K) δ=9.67 (s, 1H), 4.19 (dd, J=6.6, 3.2 Hz, 1H), 3.52 (ddd, J=25.7, 10.0, 5.7 Hz, 2H), 2.44–2.47 (m, 1H), 1.78–1.87 (m, 1H), 1.07 (d, J=7.0 Hz, 3H), 0.87 (d, J=7.0 Hz, 3H), 0.86 (s, 9H), 0.82 (s, 9H), 0.03 (s, 3H), 0.00 (2s, 6H), −0.05 (s, 3H).

Stage 8.2: A solution of 2-[bis-(2,2,2-trifluoroethyl)]-phosphono propionic acid ethyl ester (0.948 g, 2.74 mmol, prepared analog to the procedure described in Synthesis 1986, 16(11) 1285–1295) and 18-crown-6 (2.0 g, 10.0 mmol) in 20 ml THF is treated with 5.5 mL (2.74 mmol) of a 0.5 M solution of KHMDS In toluene at −78° C. After 5 min a solution of the aldehyde of stage 8.1 (1.029 g, 2.74 mmol) in 8 ml THF is added dropwise over 15 min. The pale yellow reaction mixture is stirred for additional 45 min at 0° C. Then 20 mL TBME and 20 mL of a sat. NH$_4$Cl solution is added followed by the addition of 10 mL of water. The layers are separated and the aqu. phase is extracted with 90 mL TBME. The combined organic layers are washed with brine and concentrated in vacuo. The residue is suspended in 10 mL of n-heptane, stirred for 10 min and filtered. The filtrate is concentrated to give the desired cis-ethylester.

Stage 8.3: A solution of the ethylester of stage 8.2 (97 mg, 0.21 mmol) in 5 mL of CH$_2$Cl$_2$ is treated with a 1.5 M solution in toluene of DIBAH (0.42 mL, 0.63 mmol, 3.0 eq.) at −78° C. under an atmosphere of argon. The reaction mixture is warmed to 0° C. with stirring for 30 min, after which it is quenched by addition of a 10% aqu. solution of H$_2$SO$_4$. The aqu. layer is extracted (3 times) with EtOAc. The combined organic layers are washed with sat. aqu. NaHCO$_3$ and sat. aqu. NaCl, then dried over MgSO$_4$, filtered, and concentrated in vacuo. Purification by FC (SiO$_2$, hexane/AcOEt 9:1) provides the desired allylic alcohol as a colorless oil.

Stage 8.4: A solution of the allylic alcohol of stage 8.3 (59 mg, 0.14 mmol) in 4 mL of a mixture of CH$_3$CN/Et$_2$O (1:3 v/v) is treated with PPh$_3$ (55 mg, 0.21 mmol, 1.5 eq.), imidazole (14 mg, 0.21 mmol, 1.5 eq.), and iodine (53 mg, 0.21 mmol, 1.5 eq.) at 0° C. under an atmosphere of argon. The resulting yellow suspension is stirred for 30 min at 0° C., after which a sat. aqu. solution of NaHSO$_3$ is added. The aqu. layer is extracted with TBME (3 times). The combined organic layers are washed with 1N HCl, sat. aqu. NaHCO$_3$ and sat. aqu. NaCl, then dried over MgSO$_4$, filtered, and concentrated in vacuo. Purification by FC (SiO$_2$, hexane/AcOEt 20:1) gives the desired allylic iodide as a slightly yellowish oil.

EXAMPLE 9

(4R)-4-Isopropyl-5,5-diphenyl-(N)-[(2R, 3S, 4s)-5-(4-methoxybenzyloxy)-2,4-dimethyl-3-(tert-butyl-dimethylsilyloxy)-valeryl]-oxazolidin-2-one A solution of the alcohol of Example 4 (3.61 g, 6.69 mmol) in 55 mL of CH$_2$Cl$_2$ is treated with SmOTf$_3$ (160 mg, 0.27 mmol, 4 mol %) at 23° C. under an atmosphere of argon. The slightly turbid solution is cooled to −20° C. and treated by dropwise addition over a period of 45 min with a solution of 4-methoxybenzyl-2,2,2-trichloroacetimidate (2.27 g, 8.03 mmol., 1.20 eq., prepared according to the method described in Tetrahedron 1999, 55, 1607–1630) in 55 mL of CH$_2$Cl$_2$. At the end of the addition, the resulting reaction mixture is stirred at −20° C. for 30 min, after witch it is warmed to −10° C. and treated with 50 mL of water. The layers are separated. The organic layer is washed with 0.5 N NaOH (50 mL) and aqu. sat. NaCl (50 mL), dried over MgSO$_4$, filtered and concentrated in vacuo. After purification by FC (SiO$_2$, hexane/AcOEt 5:1), the title compound is obtained as a colorless oil. $^1$H-NMR (CDCl$_3$, 300 MHz, 300K) δ=7.50–7.22 (m, 12H), 6.83–6.78 (m, 2H), 5.39 (d, J=3.3 Hz, 1H), 4.00–3.83 (m, 4H), 3.78 (s, 3H), 3.08 (dd, J=9.4, 6.5 Hz, 1H), 2.72 (dd, J=9.4, 7.1 Hz, 1H), 1.98 (heptupletd, J=6.8, 3.3 Hz, 1H), 1.60 (m, 1H), 1.25 (d, J=6.5 Hz, 3H), 0.86 (d, J=7.0 Hz, 3H), 0.81 (s, 9H), 0.76 (d, J=6.8 Hz, 3H), 0.70 (d, J=7.0 Hz, 3H), 0.00 (s, 3H), −0.02 (s, 3H).

EXAMPLE 10

(4R)-4-isopropyl-5,5-diphenyl-(N)-[(2R, 3S, 4S)-3-hydroxy-5-(4-methoxybenzyloxy)-2,4-dimethyl-valeryl]-oxazolidin-2-one A solution of the PMB ether of Example 9 (162 mg, 0.25 mmol) in 5 mL of CH$_3$CN at 23° C. is treated with 0.5 mL of 48% aqu. HF. After stirring for 24 h, the reaction is quenched with sat. aqu. NaHCO$_3$ and extracted with TBME (3 times). The combined organic layers are washed with sat. aqu. NaHCO$_3$ and sat. aqu. NaCl, dried over MgSO$_4$, filtered, and concentrated in vacuo. After purification by FC (SiO$_2$, heptane/AcOEt 3:1), the title compound is obtained as a colorless oil. $^1$H-NMR (CDCl$_3$, 300 MHz, 300K) δ 7.45–7.05 (m, 12H), 6.85–6.75 (m, 2H), 5.26 (d, J=3.5 Hz, 1H), 4.24 (d, J=11.5 Hz, 1H), 4.15 (d, J=11.5 Hz, 1H), 3.73 (s, 3H), 3.70 (qd, J=6.9, 5.4 Hz, 1H), 3.32 (m. 1H), 3.15 (d, J=5.0 Hz, 1H), 3.05 (dd, J=9.3, 4.4 Hz, 1H), 2.97 (dd, J=9.3, 5.1 Hz, 1H), 1.90 (heptupletd, J=6.8, 3.5 Hz, 1H), 1.58–1.40 (m, 1H), 1.22 (d, J=6.9 Hz, 3H), 0.80 (d, J=7.0 Hz, 3H), 0.75 (d, J=7.0 Hz, 3H), 0.71 (d, J=6.8 Hz, 3H); HRMS (ESI) m/z 568.2671 ([M+Na]$^+$; calcd. for C$_{33}$H$_{39}$NO$_6$: 568.2671).

EXAMPLE 11

(4R)-4-Isopropyl-5,5-diphenyl-(N)-[2-((1S, 3R, 6S)-3-(4-methoxyphenyl)-6-methyl-2,4-dioxacyclohex-1-yl)-(2R)-propionyl]-oxazolidin-2-one To a solution of the alcohol of Example 10 (54 mg, 0.10 mmol) in 1.0 mL of CH$_2$Cl$_2$ at 0° C. under an atmosphere of argon, 4 Å molecular sieve (55 mg) and DDQ (30 mg, 0,13 mmol, 1.3 eq.) are added sequentially in one portion. The resulting deep green reaction mixture is stirred at 0° C. for 15 h. A precipitate is formed. After removal of the precipitate by filtration, concentration in vacuo and PTLC (SiO$_2$, 10×20 cm plate, heptane/AcOEt 2:1), the title compound is obtained as a colorless oil. $^1$H-NMR (CDCl$_3$, 300 MHz, 300K) δ 7.40–7.15 (two m, 8H), 7.22 (d, J=8.7 Hz, 2H), 7.07–6.94 (m, 2H), 6.82 (d, J=8.7 Hz, 2H), 5.22 (d, J=3.4 Hz, 1H), 4.49 (s, 1H), 4.00 (qd, J=6.9, 3.4 Hz, 1H), 3.85 (dd, J=11.2, 4.6 Hz, 1H), 3.75 (s, 3H), 3.13 (t, J=11.2 Hz, 1H), 3.11 (dd, J=9.7, 3.4 Hz, 1H), 1.93 (heptupletd, J=6.8, 3.4 Hz, 1H), 1.84–1.70 (m, 1H), 1.19 (d, J=6.9 Hz, 3H), 0.85 (d, J=7.0 Hz, 3H), 0.72 (d, J=6.8 Hz, 3H), 0.53 (d, J=6.8 Hz, 3H).

EXAMPLE 12

(4R)-4-Isopropyl-5,5-diphenyl-(N)-[2-((1S, 3R, 6S)-3-(4-methoxyphenyl)-6-methyl-2,4-dioxacyclohex-1-yl)-(2R)-propionyl]-oxazolidin-2-one A solution of 9.20 g of the diol of Example 6 (21.6 mmol) in 150 mL of CH$_2$Cl$_2$ at ambient temperature is treated sequentially with 2.8 g of amberlyst 15 and 4.83 g of anisaldehyde dimethyl acetal (24.9 mmol, 1.22 eq.). The resulting reaction mixture is stirred for 2.5 h, after which it is filtered. The filtrate is concentrated in vacuo to give the desired acetal as a crude residue.

EXAMPLE 13

(3R, 4R)-3-hydroxy-4-((1S, 3R, 6S)-3-(4-methoxyphenyl)-6-methyl-2,4-dioxacyclohex-1-yl)-valeric acid tert-butyl ester To a solution of 825 μL of diisopropylamine (5.84 mmol, 2.9 eq.) in 13 mL of a mixture of THF/HMPA (85:15 v/v) at 0° C. under an atmosphere of argon is added 3.65 mL of BuLi (1.6 M in hexanes, 5.8 mmol, 2.9 eq.). After 15 min at 0° C., the reaction mixture is cooled to −78° C. and treated with 810 μL of tert-butyl acetate (6.0 mmol, 3.0 eq.). After 30 min at −78° C., the reaction mixture is treated by dropwise addition over a period of 10 min with a solution of 529 mg of the aldehyde of stage 13.2 (2.00 mmol) in 9 mL of THF/HMPA (85:15 v/v). After 15 min at −78° C., the reaction mixture is poured onto 40 mL of sat. aqu. $NH_4Cl$. The aqu. layer is extracted with TBME (3×40 mL). The combined organic layers are washed with sat. aqu. $NH_4Cl$ (30 mL), sat. aqu. NaCl (30 mL), dried over $MgSO_4$, filtered, and concentrated in vacuo. After purification by FC ($SiO_2$, hexane/AcOEt 4:1), the title compound is obtained as a colorless oil. $^1$H-NMR ($CDCl_3$, 300 MHz, 300K, mixture of epimers, ratio=3:1) major epimer: δ 7.37 (d, J=8.8 Hz, 2H), 6.85 (d, J=8.8 Hz, 2H), 5.47 (s, 1H), 4.26–4.19 (m, 1H), 4.09 (dd, J=11.3, 4.7 Hz, 1H), 3.78 (s, 3H), 3.70 (dd, J=10.0, 2.0 Hz, 1H), 3.51 (t, J=11.1 Hz, 1H), 2.51 (dd, J=15.5, 8.2 Hz, 1H), 2.39 (dd, J=15.5, 5.0 Hz, 1H), 1.98–2.17 (m, 1H), 1.92–1.78 (m, 1H), 1.44 (s, 9H), 1.04 (d, J=7.1 Hz, 3H), 0.74 (d, J=6.7 Hz, 3H); minor epimer: δ 7.34 (d, J=8.9 Hz, 2H), 6.86 (d, J=8.9 Hz, 2H), 5.48 (s, 1H), 4.08 (dd, J=11.3, 4.7 Hz, 1H), 4.06–3.97 (m, 1H), 3.91 (dd, J=10.1, 1.8 Hz, 1H), 3.79 (s, 3H), 3.52 (t, J=11.1 Hz, 1H), 2.58 (dd, J=16.0, 3.8 Hz, 1H), 2.39 (dd, J=16.0, 8.7 Hz, 1H), 1.98?2.17 (m, 1H), 1.92–1.78 (m, 1H), 1.45 (s, 9H), 0.99 (d, J=7.1 Hz, 3H), 0.73 (d, J=6.8 Hz, 3H); MS (EI) m/z783 (5, [2 M+Na]$^+$), 403 (100, [M+Na]$^+$), 347 (25, [M+Na—$C_2H_8$]$^+$).

Stage 13.1: To a solution of 12.62 g of the crude acetal of Example 11 in 60 mL of THF at 78° C. under an atmosphere of argon is added over a period of 30 min 62 mL of a 1 M solution of $LiAlH_4$ in THF (62 mmol). After 3 h of stirring at −78° C., the reaction mixture is warmed to 0° C. and treated sequentially with 2.4 mL of water, 2.4 mL of 15% aqu. NaOH, and 7.1 mL of water. The resulting precipitate is removed by filtration and washed with THF (2×10 mL). The filtrate is collected and concentrated in vacuo to half of its initial volume. A white precipitate is formed during the concentration. Heptane (100 mL) is added and more of the precipitate is formed. The suspension is evaporated in vacuo to half of its initial volume, stirred at 0° C. for 30 min and filtered. The residue is washed with heptane (3×10 mL). The filtrate is collected and concentrated in vacuo to give the crude desired alcohol as a yellowish oil.

Stage 13.2: A solution of 3.10 g of oxalyl chloride (24 mmol) in 40 mL of $CH_2Cl_2$ at −78° C. under an atmosphere of argon is treated sequentially by dropwise addition of a solution of 4.22 g of DMSO (54 mmol) in 16 mL of $CH_2Cl_2$ and a solution of the crude alcohol of stage 13.1 (6.20 g) in 30 mL of $CH_2Cl_2$. The resulting reaction mixture is stirred at −78° C. for 30 min. The reaction mixture is then treated by dropwise addition of 18.5 mL of diisoproylethylamine (108 mmol) and is stirred at −78° C. for 1 h before being warmed to 0° C. Water (70 mL) is added and the aqu. layer is extracted with $CH_2Cl_2$ (2×40 mL). The combined organic layers are washed with sat. aqu. NaCl (2×50 mL), dried over $MgSO_4$, filtered, and concentrated in vacuo. After purification by FC ($SiO_2$, heptane/AcOEt 3:1), the desired aldehyde is obtained as a colorless oil. $^1$H-NMR ($CDCl_3$, 300 MHz, 300K) δ 9.76 (s, 1H), 7.33 (d, J=8.8 Hz, 2H), 6.86 (d, J=8.8 Hz, 2H), 5.48 (s, 1H), 4.15 (dd, J=11.3, 4.7 Hz, 1H), 4.07 (dd, J=10.1, 2.50 Hz, 1H), 3.79 (s, 3H), 3.58 (dd, J=11.3 Hz, 1H), 2.58 (qd, J=7.1, 2.5 Hz, 1H), 2.10 (ddqd, J=11.3, 10.1, 6.7, 4.7, Hz, 1H), 1.24 (d, J=7.1 Hz, 3H), 0.81 (d, J=6.7 Hz, 3H).

EXAMPLE 14

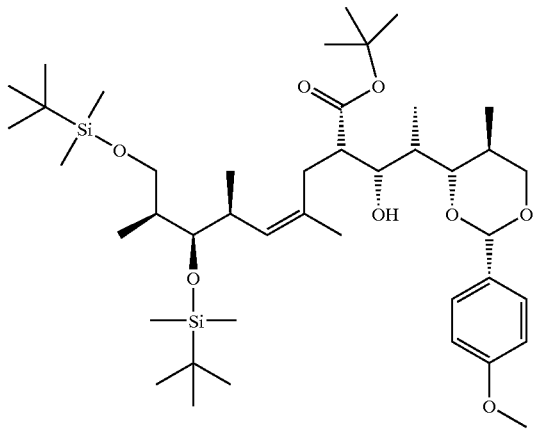

To a stirred solution of LDA (0.71 mmol, prepared from 0.77 mmol of diisopropylamine and 0.71 mmol of Buli 1.6 M in hexanes at 0° C.) in THF (0.30 mL) at −50° C. under an atmosphere of argon is added a solution of the product from Example 13 (118 mg, 0.31 mmol) in THF (0.30 mL). The reaction mixture is allowed to warm to −10° C. and stirred at that temperature for 10 min. The reaction mixture is then cooled to −50° C. and stirred at that temperature for 30 min. A solution of the product from stage 8.4 (244 mg, 0.42 mmol) in a mixture of THF (0.10 mL) and HMPA (0.10 mL) is added. The reaction mixture is stirred for 2 h at −50° C. before being diluted with TBME (2 mL) and poured into an aqu. sat. solution of $NH_4Cl$ (2 mL). The reaction mixture is then partitioned between $NaHCO_3$ (2×5 mL) and TBME (2×5 mL). The combined organic extracts are washed with NaCl (5 mL), dried ($MgSO_4$) and concentrated in vacuo. Filtration over $SiO_2$ (5% EtOAc/Hexanes) provides the product as a colourless oil; MS (EI) m/z801 (100, [M+Na]$^+$).

EXAMPLE 15

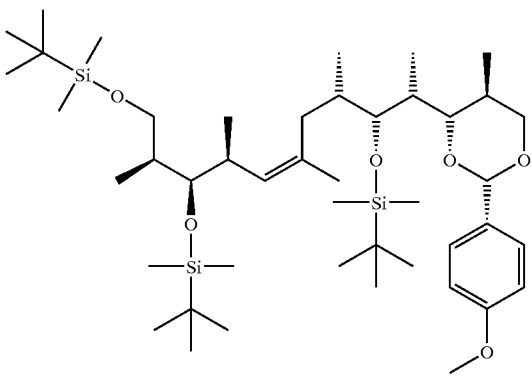

To a stirred solution of the crude product of stage 15.3 (350 mg, 0.39 mmol) in THF (10 mL) at −78° C. is added LiAlH$_4$ (4.0 mL of a 1M/THF solution, 4.00 mmol) and allowed to gradually warm to −10° C. over 1.5 h. The reaction is then quenched by the addition of MeOH (2 mL) and partitioned between potassium sodium tartrate (15 mL) and TBME (3×50 mL). The combined organic extracts are dried (MgSO$_4$) and concentrated in vacuo. Flash chromatography (95% EtOAc/hexane) gives the desired compound as a colourless solid; IR (KBr): v$_{max}$ 2959 s, 2930 s, 2857 s, 1472 m, 1462 m, 1250 s, 1113 m, 1083 s, 1062 s, 1038 m, 1019 s, 1005 w, 856 w, 835 s, 774 s; $^1$H-NMR (CDCl$_3$, 500 MHz, 298K) δ 7.85 (dt, J=9.0, 2.0 Hz, 2H), 6.88 (dt, J=9.0, 2.0 Hz, 2H), 5.39 (s, 1H), 5.07 (d, J=10.0 Hz, 1H), 4.10 (dd, J=11.0, 4.5 Hz, 1H), 3.80 (s, 3H), 3.63 (dd, J=5.0, 2.0 Hz, 1H), 3.62 (dd, J=10.0, 5.0 Hz, 1H), 3.52 (dd, J=10.0, 2.0 Hz, 1H), 3.48 (t, J=11.5 Hz, 1H), 3.43 (t, J=5.5 Hz, 1H), 3.36 (dd, J=10.0, 8.0 Hz, 1H), 2.51 (m, 1H), 2.34 (t, J=12.0 Hz, 1H), 2.06 (m, 1H), 1.99 (m, 1H), 1.88 (td, J=7.0, 1.5 Hz, 1H), 1.80 (m, 1H), 1.71 (br d, J=11 Hz, 1H), 1.58 (s, 3H), 1.02 (d, J=7.0 Hz, 3H), 0.91 (d, J=7 Hz, 3H), 0.91 (s, 9H), 0.90 (s, 9H), 0.89 (d, J=7 Hz, 3H), 0.889 (s, 9H), 0.76 (d, J=7.0 Hz, 3H), 0.75 (d, J=6.50 Hz, 3H), 0.05 (s, 3H), 0.04 (s, 3H), 0.02 (s, 9H), 0.01 (s, 3H); $^{13}$C-NMR (CDCl$_3$, 125 MHz, 300K) δ 131.8, 131.7, 127.5, 114.5, 113.6, 101.2, 83.6, 78.6, 77.7, 73.5, 65.5, 55.4, 41.5, 38.3, 37.5, 35.4, 34.0, 31.0, 26.1, 26.0, 25.8, 23.3, 18.6, 18.5, 16.8, 13.8, 12.8, 12.3, 11.0, 5.9, −3.3, −3.4, −3.5, −3.6, −3.8, −5.1; MS (EI) m/z: 829 (7, [M+Na]$^+$), 826 (17, [2M+Ca]$^{2+}$), 377 (90), 313 (100).

Stage 15.1: To a stirred solution of the crude product of Example 14 (400 mg, 0.51 mmol) in CH$_2$Cl$_2$ (10 mL) at −78° C. Et$_3$N (714 μL, 5.13 mmol) is added, followed by addition of TBDMSOTf (586 μL, 2.55 mmol). The reaction mixture is allowed to warm to RT and stirred for 4 h. The reaction mixture is then partitioned between NaHCO$_3$ (20 mL) and CH$_2$Cl$_2$ (3×50 mL). The combined organic extracts are dried (MgSO$_4$) and concentrated in vacuo. Filtration over SiO$_2$ (5% EtOAc/Hexanes) gives the crude product as a colourless oil; MS (EI) m/z 915 (100, [M+Na]$^+$).

Stage 15.2: To a stirred solution of the crude product of stage 15.1 (561 mg, 0.63 mmol) in THF (15 mL) at −78° C. is added LiAlH$_4$ (6.30 mL of a 1M/THF solution, 6.30 mmol). The reaction mixture is allowed to gradually warm to −15° C. over 1 h. The reaction mixture is then quenched by the careful addition of a aqu. solution of potassium sodium tartrate (30 mL) and stirred vigorously at RT. After 30 min, the layers are separated and the aqu. layer is extracted with TBME (3×100 mL). The combined organics are dried (Na$_2$SO$_4$) and concentrated in vacuo. Filtration over SiO$_2$ (5–30% EtOAc/Hexanes) provides the desired alcohol as a colourless oil; MS (EI) m/z 923 (100, [M+Na]$^+$).

Stage 15.3: To a stirred solution of the crude product of stage 15.2 (400 mg, 0.49 mmol) in CH$_2$Cl$_2$ (10 mL) at RT is added Et$_3$N (338 μL, 2.43 mmol) and methanesulfonylchloride (58 μL, 0.74 mmol). After 20 h the mixture is partitioned between NaHCO$_3$ (15 mL) and CH$_2$Cl$_2$ (3×20 mL). The combined organic extracts are dried (Na$_2$SO$_4$) and concentrated in vacuo. Filtration over SiO$_2$ (10–20% EtOAc/Hexanes) gives the crude product as a colourless oil; MS (EI) m/z 891 (100, [M+Na]$^+$).

What is claimed is:

1. A process for preparing a substituted alkene of formula I

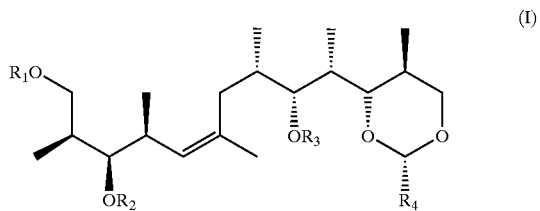

wherein

R$_1$, R$_2$ and R$_3$ are independently of each other a protecting group for a hydroxy group or hydrogen and R$_4$ is phenyl which is unsubstituted or mono- or disubstituted by alkoxy, in which process a carboxylic ester of the formula III

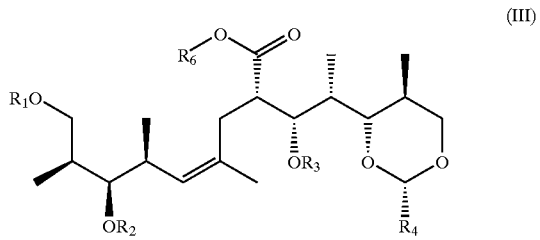

wherein R$_1$, R$_2$ and R$_3$ are all protecting groups for a hydroxy group which protecting groups can be identical or different, R$_6$ is alkyl or arylalkyl, and R$_4$ has the meaning as defined for the compound of formula I, is first reduced, to obtain alcohol of the formula IV

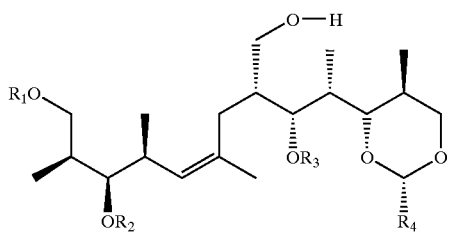
(IV)

wherein $R_1$, $R_2$, $R_3$ and $R_4$ have the meanings as defined for the compound of formula III, is further reacted with a compound of formula V $R_5SO_2Hal$ (V)

wherein $R_5$ is alkyl or aryl which is unsubstituted or substituted by alkyl, and Hal represent halogen, and the obtained sulfonate of formula II

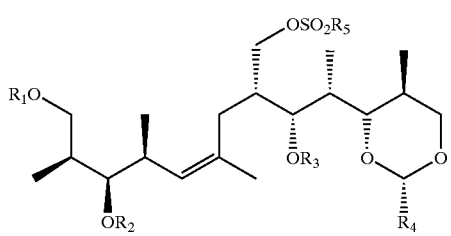
(II)

wherein $R_1$, $R_2$, $R_3$ and $R_4$ have the meanings as defined for the carboxylic ester of formula III and $R_5$ is alkyl or aryl which is unsubstituted or substituted by alkyl, is further reduced, and, if desired, one, two or all protecting groups $R_1$, $R_2$ and $R_3$ are detached by methods known in the art to obtain a compound of formula I.

2. A process for preparing a carboxylic ester of formula II

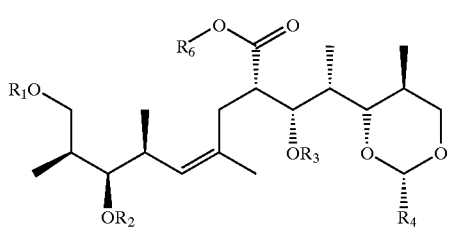
(III)

wherein $R_1$ and $R_2$ are protecting groups for a hydroxy group which protecting groups can be identical or different or hydrogen, $R_3$ is hydrogen, $R_4$ is phenyl which is unsubstituted or mono- or disubstituted by alkoxy, and $R_6$ is alkyl or arylalkyl, in which process an allyl halide of the formula VI

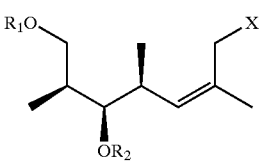
(VI)

wherein $R_1$ and $R_2$ have the meanings as defined for a carboxylic ester of formula III and X is halogen, is reacted with a carboxylic ester of formula VII (VII)

wherein $R_3$, $R_4$ and $R_6$ have the meanings as defined for a carboxylic ester of formula III in the presence of a base, and afterwards, if desired, one or all protecting groups $R_1$ and $R_2$ are split off to obtain a compound of formula III.

3. A process according to claim 1 wherein $R_1$ and $R_2$ are identical and $R_1$, $R_2$ and $R_3$ are silyl protecting groups.

4. A sulfonate of formula II (II)

wherein $R_1$, $R_2$ and $R_3$ are all protecting groups for a hydroxy group which protecting groups can be identical or different, $R_4$ is phenyl which is unsubstituted or mono- or disubstituted by alkoxy, and $R_5$ is alkyl or aryl which is unsubstituted or substituted by alkyl.

5. A sulfonate of formula II according to claim 4 wherein $R_1$ and $R_2$ are identical, $R_1$, $R_2$ and $R_3$ are benzyl or silyl protecting groups, $R_4$ is phenyl which is unsubstituted or mono- or disubstituted by alkoxy, and $R_5$ is lower alkyl or phenyl which is substituted by lower alkyl.

6. A sulfonate of formula II according to claim 4 wherein $R_1$ and $R_2$ and $R_3$ are tert-butyl dimethylsilyl, $R_4$ is phenyl which is unsubstituted or monosubstituted by lower alkoxy and $R_5$ is lower alkyl or phenyl which is monosubstituted by lower alkyl.

7. A carboxylic ester of formula III

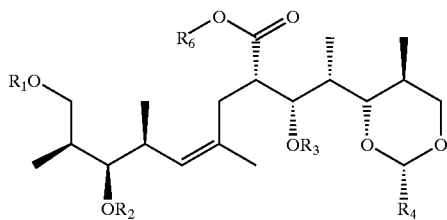

(III)

wherein $R_1$ and $R_2$ are protecting groups for a hydroxy group which protecting groups can be identical or different, $R_3$ is a protecting group for a hydroxy group or hydrogen, $R_4$ is phenyl which is unsubstituted or mono- or disubstituted by alkoxy, and $R_6$ is alkyl or arylalkyl.

8. A carboxylic ester of formula III according to claim 7 wherein $R_1$ and $R_2$ are identical, $R_1$, $R_2$ and $R_3$ are silyl protecting groups and $R_6$ is lower alkyl.

9. An alcohol of formula IV

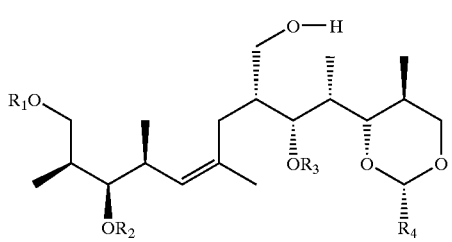

(IV)

wherein $R_1$, $R_2$ and $R_3$ are all protecting groups for a hydroxy group which protecting groups can be identical or different and $R_4$ is phenyl which is unsubstituted or mono- or disubstituted by alkoxy.

* * * * *